United States Patent [19]

Janisiewicz et al.

[11] Patent Number: 4,975,277
[45] Date of Patent: Dec. 4, 1990

[54] **BIOLOGICAL CONTROL OF POSTHARVEST ROTS IN FRUITS USING *PSEUDOMONAS CEPACIA* AND PYRROLNITRIN PRODUCED THEREFROM**

[75] Inventors: Wojciech J. Janisiewicz, Martinsburg, W. Va.; James Roitman, Berkeley, Calif.

[73] Assignee: United States of America, Washington, D.C.

[21] Appl. No.: 227,211

[22] Filed: Aug. 2, 1988

[51] Int. Cl.$^5$ .............................................. C12R 1/38
[52] U.S. Cl. ................................... 424/93; 435/253.3
[58] Field of Search ........................ 424/93; 435/253.3

[56] References Cited

PUBLICATIONS

P. L. Pusey et al., "Postharvest Biological Control of Stone Fruit Brown Rot by *Bacillus subtilis*", *Plant Disease* 68: 753–756 (1984).
V. Singh et al., "*Bacillus subtilis* as a Control Agent Against Fungal Pathogens of Citrus Fruit", *Trans, Br. Mycol Soc. 83:* 487–490 (1984).
A. P. de Matos, "Chemical and Microbiological Factors Influencing the Infection of Lemons by Geotrichum and *Penicillium digitatum*", Ph.D. Dissertation, University of California Riverside, (1983).
A. Tronsomo et al., "The Use of Trichoderma Species to Control Strawberry Fruit Rots", Neth. J. Pl. 83 (Supp. I): 449–455 (1977).
A. Tronsomo et al., "Biological Control of *Botrytis cinerea* on Apple", Plant Dis. 64:1009 (1980).
J. P. Sleesman et al., "Microbial Antagonists of *Bipolaris maydis*", Phytopathology 66: 1214–1218 (1976).
S. O. Kawamoto et al., "Protection of Onion Seedlings from *Fusarium oxysporum F. SP. Cepae* by Seed and Soil Infestation with *Pseudomonas cepacia*", Plant Dis. Reptr. 60: 189–191 (1976).
C. L. Wilson et al., "Potential for Biological Control of Postharvest Plant Disease", *Plant Disease* 69: 375–378 (1985).
W. J. Janisiewicz, "Biocontrol of Two Postharvest Diseases of Apples with a Yeast", Phytopathol. 76:1133 (1986).

*Primary Examiner*—Howard E. Schain
*Assistant Examiner*—Choon Koh

[57] ABSTRACT

A process for biologically controlling postharvest disease in pome fruits using an isolate of *Pseudomonas cepacia* having the identifying characteristics of NRRL B18388. The organisms are isolated from the surface of apple leaves and are useful to control a variety of fruit-rot pathogens in a variety of pome fruits. Also disclosed is a process for controlling postharvest diseases in pome fruit using the antifungal compound, pyrrolnitrin.

4 Claims, No Drawings

BIOLOGICAL CONTROL OF POSTHARVEST ROTS IN FRUITS USING *PSEUDOMONAS CEPACIA* AND PYRROLNITRIN PRODUCED THEREFROM

BACKGROUND OF THE INVENTION

1. Field of the Invention

The present invention relates to the biological control of postharvest diseases in fruit. More particularly, this invention relates to a method for biologically controlling postharvest rots on fruits using a strain of *Pseudomonas cepacia*, "*P. cepacia.*" and the antifungal compound, pyrrolnitrin, produced therefrom.

2. Description of Prior Art

Postharvest diseases of fruit cause 15 to 25% losses yearly in the fruit industry worldwide. Fungicides, the major weapon in combatting these diseases, are often ineffective and pose hazards to humans and the environment. Therefore, a critical need exists for new methods to control postharvest diseases.

Recently, it has been shown that the postharvest treatment of fruit with antagonistic microorganisms is an effective approach to the control of postharvest rots. Remarkable success was shown in the control of brown rot in peaches caused by *Monilinia fructicola* (Wint.) Honey with *Bacillus subtilis*. Pusey et al. [Plant Dis. 68: 753–756 (1984)]. De Matos was able to reduce mold incidence from 35% to 8% when a species of Trichoderma was inoculated with *Penicillium digitatum* into lemon peel. De Matos, Ph.D Dissertation, University of California, Riverdale, (1983). Singh and Deverall demonstrated biocontrol with bacterial antagonists to the citrus pathogens *Alternaria citri* Pierce, *Geotrichum candidum* link. ex Pers., and *P. digitatum*. Singh et al. [Trans. Br. Mycol. Soc. 83: 487–490 (1983)]. Dipping wounded citrus fruit in suspensions of bacterial cells, particularily a strain of *Bacillus subtilis* (Ehrenber) Cohn, delayed decay by the three rot pathogens.

*Trichoderma viride* Pers. & S. F. Gray applied to strawberry plants in the field was shown to partially control gray-mold on strawberry fruits after harvest. Tronsmo et al. [Neth. J. Plant Pathol. 83(suppl. 1): 449–455 (1977)]. Also, partial control of rot in apples caused by *B. cinerea* flower infection was obtained by applying conidia *T. harzianium* Rifai to apple trees during bloom. Control was comparable to prior known fungicidal treatments. Tronsmo et al. [Plant Dis. 64:1009 (1980)].

*P. cepacia* has been reported to reduced southern maize leaf blight caused by *Bipolaris maydis* in greenhouse tests, Sleesman et al. [Phytopathology 66: 1214–1218 (1976)], decrease peanut Cercospora leaf spot and tobacco Alternaria leaf spot in the field, Spur [Phytopathology News (Abstract) 74:17 (1978)], and to control damping off of onion seedlings by *Fusarium oxysporum* f.sp. *cepae*. Kawamoto et al. [Plant Dis. Rep. 60: 189–191 (1976)].

SUMMARY OF THE INVENTION

I have now discovered an isolate of *P. cepacia* which is highly effective to control a variety of fruit-rot pathogens which affects several species of fruit. The principle mode of action of this bacterium is the production of pyrrolnitrin 3-chloro-4-(3-chloro-2-nitrophenyl) pyrrole. Pyrrolnitrin is a powerful antifungal agent and is highly effective to inhibit the development of postharvest diseases-causing pathogens in a safe and economical manner.

Viable cultures of the isolate of *P. cepacia* useful in the present invention have been deposited with the culture collection at The Northern Regional Research Center, U.S. Department of Agriculture, Peoria, Ill. 61604, under the acquistion number NRRL B-18388. Progenies of the isolate will be available during the pendency of the patent application to one determined by the Commissioner of Patents and Trademarks to be entitled thereto under 37 CFR 1.14 and 35 USC 122. All restrictions on the availability of progenies of the isolate to the public will be irrevocably removed upon the granting of the patent of which the isolate is the subject.

Accordingly, it is an object of the present invention to provide a biological control agent which is safe and highly effective to control a variety of postharvest diseases in a variety of fruits.

It is also a object of the present invention to provide a novel antifungal agent which inhibits the development of variety of postharvest disease-causing pathogens in a variety of pome fruits.

In accordance with my invention, pome fruits are subjected to an aqueous suspension of isolate NRRL B-18388 in an amount effective to inhibit of the development of a targeted postharvest disease-causing pathogen. In the alternative, the pome fruits are subjected to an aqueous solution of pyrrolnitrin in an amount effective to inhibit the development of the pathogen.

DETAILED DESCRIPTION OF THE INVENTION

Isolate NRRL B-18388 is isolated from apple leaves by repeatedly washing the leaves with a suitable aqueous buffer, i.e. a phosphate buffer and the like. Thereafter, the organisms are plated and grown on a nutritionally rich medium sufficient to support growth of the organism. For optimum growth, the preferred medium is either nutrient yeast dextrose broth (NYDB) or nutrient yeast dextrose agar (NYDA).

Isolate NRRL B-18388 has the following characteristic description: Colonies are yellow or whitish in color, rod-shaped, 0.8–1.0 by 1.6–3.3 $\mu$m, singly or in pairs. Accumulate poly-$\beta$-hydroxybutyrate granules as intracellular carbon reserve, especially in nitrogen-deficient media. Motile with polar multrichous flagellation (one to three flagella).

Growth of NRRL B-18388 is effected under aerobic conditions at any temperature satisfactory for growth of the organisms, i.e. from about 10° C. to about 30° C. The preferred temperature range is about 20° C. to 25° C. The pH of the nutrient medium is about neutral, i.e. 6.7 to 7.2. The incubation time is that time necessary for the organisms to reach a stationary phase of growth, preferably, from about 20 to 28 hours.

Isolate NRRL B-18388 may be grown in any conventional shake flask for small fermentation runs. For large scale operations, it is convenient to carry out the culture in a fermentation tank, while applying agitation and aeration to the inoculated liquid medium. Following incubation, the organisms are harvested by conventional sedimentary methodology, i.e. centrifugation or filtering. Cultures are stored until use.

Isolate NRRL B-18388, and pyrrolnitrin produced therefrom, are useful to control a variety of fruit-rot pathogens which causes postharvest diseases in fruits. Exemplary species of fruit-rot pathogens include, but are not limited to, *Botyrtis cinerea* "*B. cinerea,*" *Penicil-*

*lium expansum* "*P. expansum,*" *Mucor sp.* and *Aspergillus sp.*

The organism of the invention, and the pyrrolnitrin produced therefrom, are useful to control postharvest diseases in a variety of pome fruit including, but not limited to, all cultivars of apples, pears, and the like. For purposes of this invention, the term "pome fruit" is used herein to designate fruits having a fleshy outer layer and a central core with seeds enclosed in a capsule.

In accordance with the invention, the fruits are treated directly with the bacterium NRRL B-18388 or with pyrrolnitrin. Pyrrolnitrin useful in the invention maybe be isolated from the bacterium itself or synthesized in accordance with the procedure as described in Nakano et al. [Tetrahedron Letters, 737 (1966)]. It is within the compass of the invention to treat the fruits with either isolate NRRL B-18388 or pyrrolnitrin alone, or in combination with other control agents useful to inhibit the development of fruit-rot pathogens on fruits. When used, these control agents should be use in an amount which as readily determined by one skilled in the arts, will not interfere with the effectiveness of the treatment of the invention to inhibit the targeted pathogens.

The bacterium NRRL B-18388 is preferably applied to the fruits in suspension with water. When grown in a liquid medium, the organism may be applied in suspension with the liquid medium. Suspensions of NRRL B-18388 may also include conventional additives such as surfactants to enhance the effectiveness of the organisms. In a like manner, pyrrolnitrin is applied to the fruits in solution with water. However, it may be necessary to first dissolve pyrrolnitrin in a more soluble medium, e.g. methy or ethyl alcohol, prior to addition to water.

Concentrations of the treatments of the invention are any concentrations which inhibit the development of the targeted fruit-rot pathogen when applied to the fruit. As will be obvious to one skilled in the arts, effective concentrations may vary depending upon such factors as (1) the type of fruit; (2) the ripeness of the fruit; (3) the concentration of pathogens affecting the fruit; (4) the type of wound on the fruit; (5) temperature and humidity; and (6) the age of the fruit-rot pathogen. Exemplary concentrations of aqueous suspension of NRRL B-18388 useful in the invention range from about $1 \times 10^7$ to $1 \times 10^8$ CFU/ml, most preferably, from about $5 \times 10^7$ to $1 \times 10^8$ CFU/ml. Exemplary concentrations of aqueous solutions of pyrrolnitrin range from 0.01 mg/ml to 0.1 mg/ml, most preferably 0.5 mg/ml to 0.1 mg/ml.

The treatments of the inventions maybe applied to fruits using conventional methods such as dipping, spraying or brushing. In addition, the treatments maybe incorporated into waxes, wraps or other protective coatings used in processing the fruits.

The fruits may be treated anytime before or after harvest. Typically, the preferred time of treatment is after harvest and prior to storage or shipment.

The following examples are intended to further illustrate the invention are not to limit the scope of the invention as defined by the claims.

EXAMPLE I

The effectiveness of *P. cepacia* NRRL B-18388 to inhibit the development of *P. expansum* and *B. cinerea* in Golden Delicious apples and Bosc pears was demonstrated.

A biologically pure culture of isolate NRRL B-18388 was obtained using the following procedure: Apple leaves were washed in 200 ml of phosphate buffer, pH 6.8, on a rotary shaker at 100 rpm for 10 minutes. The washings were discarded, and the leaves were washed a second time for 10 minutes with sonication for 30 seconds in a Branosomic 521 sonicator (Branson Co., Shelton, Conn.) at the beginning of the wash. Washings from sonicated samples were plated on NYDA (0.1 ml/plate) and incubated for 24 hours at 23° C.±2° C. Appearing colonies were isolated and purified using standard purification techniques.

Isolate NRRL B-18388 was grown in flasks containing nutrient yeast dextrose broth (NYDB) on a reciprocal shaker at 24° C. for 24 hours. The culture was centrifuged at 10,000 rpm for 10 minutes and the resulting pellet was suspended in water at various concentrations. Concentrations of the aqueous suspensions were adjusted on a spectrophotometer.

Golden Delicious Apples: Golden Delicious apples were wounded at the equator (one wound of 3 mm in diameter and 3 mm deep per apple). The wounds were inoculated with 20 l of an aqueous suspension of NRRL B-18388. Shortly, thereafter, the wounds were inoculated with 20 $\mu$l of aqueous conidia suspensions of *P. expansum* or *B. cinerea*. The concentration of the conidia suspensions ranged from $1 \times 10^3$ to $1 \times 10^5$ conidia/ml in ten fold increases. Concentrations of isolate NRRL B-18388 in aqueous suspension varied as shown in Table I. Control fruits were inoculated with aqueous conidia suspensions of *P. expansum* or *B. cinerea* only.

Treated apples were incubated at 23±1° C. and 76±4% relative humidity for 7 days, after which the diameter of lesions was measured. The experiment was arranged in a randomized block design. Each apple constituted a single replicate, and each treatment was replicated 6 times. The separation of means was measured using the appropriate Least Significant Difference (LSD) analysis at P=0.05.

The results were recorded in Table I.

Bosc Pears: Bosc pears were treated in a similar manner as hereinaforedescribed for Golden Delicious Apples, except that two wounds were made on each fruit, one closer to the stem and the other closer to the calyx end. The diameter of the lesion was measured after 5 days. Each pear constituted a single replicate and each treatment was replicated 6 times.

The results were recorded in Table I.

As shown in Table I, *P. cepacia* NRRL B-18388 strongly inhibited the development of gray-mold and blue-mold lesions on apples and pears. The greatest activity was observed on apples where no lesion developed on fruit treated with the two highest concentrations of *P. cepacia* NRRL B-18388 inoculated with $1 \times 10^3$ or $1 \times 10^4$ conidia/ml of *B. cinerea*. At $10^5$ conidia/ml only small lesions developed. In the case of *P. expansum*, no treatment resulted in complete lesion suppression although significant reduction in lesion size occurred in almost all treatments. On Bosc pears the greatest protection occurred on fruit treated with the highest concentration of *P. cepacia* NRRL B-18388 and the lowest concentration of *B. cinerea*. At the two highest pathogen inoculum levels and at all NRRL B-18388 concentrations, lesions were large and only slightly different from the control. Although total inhibition did not occur, significant reduction in lesion size was observed on pears inoculated with aqueous conidia suspensions of *P. expansum* spores.

EXAMPLE II

The effectiveness of pyrrolnitrin to inhibit the development of B. cinerea and P. expansum was demonstrated.

Isolation of Pyrrolnitrin: P. cepacia NRRL B-18388 was grown in 250 ml of NYDB in 2800 ml flasks for 3 days at ambient temperature on a rotary shaker at 250 rpm. The culture was centrifuged at 10,000 rpm for 10 minutes. The resulting pellet of bacterial cells was suspended in water, sonicated for 5 minutes at 350 watts with a Branson Sonnifier 350 equipped with 1.3 cm horn, and centrifuged again at 10,000 rpm for 10 minutes. The pellet was discarded, and the supernatant was stirred with Amberlite XAD-7 (Rohm & Haas, Philadelphia, Pa.) resin for 3 hours (150 ml of resin per liter of solution). The resin was collected by filtration on a coarse sintered glass funnel and washed with deionized water until clear. Thereafter the wash was discarded, and the material retained on the resin was washed off with methanol. The methanol was evaporated on a rotary evaporator, and the residue was resuspended in methanol and filtered. The filtrate was dried by rotary evaporation, redissolved in methanol, filtered through a 0.45 $\mu$ filter, and separated by preparative high-pressure liquid chromatography (HPLC). The HPLC was equipped with a reverse phase column (21.4 mm $\times$ 250 mm) and a 50-mm guard column. Isoratic elution was used with 60% acetonitrile and 40% water at a flow rate of 2 ml/minutes. The detector was set at 254 nm. Twenty fractions were collected at 1 minute intervals.

The fractions were dried by rotary evaporation and assayed for antifungal activity using the agar diffusion test: The fractions were dissolved in methanol, diluted with water, and placed in a well (1 cm diameter) made in the center of petri plates containing 15 ml of NYDA. After incubation for 24 hr at 24° C., the plates were seeded with an aqueous spore suspension ($1 \times 10^6$ conidia/ml) of two fungi (B. cinerea or P. expansum), and again incubated for 48 hr at 24° C., after which the plates were evaluated for zones of fungal growth inhibition. Antifungal activity was observed in fraction #14 which eluted at about 14 minutes. Further purification was accomplished by drying fraction #14 on a rotary evaporator and rechromatographing by HPLC through and IBM cyano column (10 mm $\times$ 250 mm) by isocratic elution with 50% chloroform and 50% hexane at a flow rate of 5 ml/minutes. Activity was observed in the fraction collected 6 minutes after sample injection. The fraction was evaporated and recrystallized from hexane. The melting point, UV spectrum, and proton NMR spectrum were in accordance with data reported for pyrrolnitrin by K. Arima et al. [I. J. Antibiotics, A18:201 (1965)].

Using the procedure as hereinbefore described, starting with Ambelite XAD-7 mixing, pyrrolnitrin was also isolated from the supernatant of the centrifuged culture of P. cepacia NRRL B-18388.

Pyrrolnitrin Activity on Apples and Pears: Pyrrolnitrin was dissolved first in methanol (1 mg of pyrrolnitrin per 1 ml of methanol) and then diluted with water to the desired concentrations. Golden Delicious apples and Bosc pears were wounded as described in Example I and 20 $\mu$l of an aqueous pyrrolnitrin solution was placed into each wound. Pathogens inoculation, incubation time and temperature, lesion measurements, and experimental design were the same as described in Example I for treatment of the fruit with cells of P. cepacia, except that the concentration of the pyrrolnitrin in aqueous solutions varied as shown in Table II.

Pyrrolnitrin was highly effective to inhibit the development of P. expansum and B. cinerea in both apples and pears. As shown in Table II, apples and pears treated with pyrrolnitrin generally showed no lesion development from P. expansum and B. cinerea. Lesions were observed only on fruit treated with the lowest concentration of pyrrolnitrin and inoculated with the two highest conidia concentrations of P. expansum for pears and the highest concentration of P. expansum for apples.

It is understood that modifications and variations maybe made to the foregoing disclosure without departing from the spirit and scope of the invention.

TABLE I

Lesion diameter (mm) on Golden Delicious apples and Bosc pears protected with Pseudomonas cepacia and inoculated with conidia suspensions of Penicillium expansum or Botrytis cinerea

| Fruit | P. cepacia conc. CFU/ml $10^7$ | Penicillium expansum conidia/ml $10^3$ | $10^4$ | $10^5$ | Botrytis cinerea conidia/ml $10^3$ | $10^4$ | $10^5$ |
|---|---|---|---|---|---|---|---|
| Apples | 0 | 41.5 | 44.8 | 43.8 | 57.5 | 35.88 | 61.7 |
|  | 1.4 | 26.5 | 23.0 | 33.7 | 14.3 | 0 | 11.0 |
|  | 2.2 | 9.8 | 30.7 | 32.7 | 22.6 | 7.3 | 12.0 |
|  | 4.0 | 4.7 | 31.5 | 33.0 | 0 | 0 | 12.0 |
|  | 11.0 | 23.7 | 30.8 | 39.2 | 0 | 0 | 4.3 |
|  | $LSD_{0.05}$ | 13.1 | 11.9 | 7.2 | 16.9 | 15.9 | 15.6 |
| Pears | 0 | 20.1 | 23.9 | 27.5 | 27.7 | 33.3 | 35.3 |
|  | 1.4 | 10.3 | 10.2 | 19.5 | 11.5 | 20.7 | 30.3 |
|  | 2.2 | 8.3 | 12.6 | 19.1 | 9.8 | 20.3 | 26.9 |
|  | 4.0 | 11.0 | 12.8 | 22.4 | 11.2 | 18.4 | 31.2 |
|  | 11.1 | 6.8 | 12.6 | 23.3 | 1.0 | 30.3 | 30.3 |
|  | $LSD_{0.05}$ | 6.1 | 6.8 | 3.0 | 5.3 | 2.4 | 3.3 |

LSD — Least significant difference

TABLE II

Lesion diameter (mm) on Golden Delicious apples and Bosc pears protected with pyrrolnitrin and inoculated with spore suspensions of Penicilium expansum or Botrytis cinerea

| Fruit | Pyrrolnitrin concentration (mg/ml) | Penicillium expansum conidia/ml $10^3$ | $10^4$ | $10^5$ | Botrytis cinerea conidia/ml $10^3$ | $10^4$ | $10^5$ |
|---|---|---|---|---|---|---|---|
| Apples | 0 | 39.3 | 40.3 | 41.7 | 18 | 30.6 | 41.5 |
|  | 0.01 | 0 | 0 | 3.2 | 0 | 0 | 0 |
|  | 0.05 | 0 | 0 | 0 | 0 | 0 | 0 |
|  | 0.1 | 0 | 0 | 0 | 0 | 0 | 0 |
| Pears | 0 | 17.8 | 19.3 | 22.3 | 21.7 | 20.8 | 30.1 |
|  | 0.01 | 0 | 2.8 | 7.6 | 0 | 0 | 0 |
|  | 0.05 | 0 | 0 | 0 | 0 | 0 | 0 |
|  | 0.10 | 0 | 0 | 0 | 0 | 0 | 0 |

We claim:

1. A process for biologically controlling postharvest disease in pome fruit comprising subjecting the fruit to an isolate of *Psuedomonas cepacia* in an amount effective to inhibit the development of the fruit-rot pathogen causing the postharvest disease, wherein the isolate of *Psuedomonas cepacia* has the identifying characteristics of isolate NRRL B-18388.

2. The process of claim 1 wherein the fruit-rot pathogen is selected from the group consisting of *Botyrtis cinerea, Penicillium expansum*, Mucor sp. and Asperigillus sp.

3. The process of claim 1 wherein the pome fruit is selected from the group consisting of apples and pears.

4. A biologically pure culture of an isolate of *Psuedomonas cepacia* having the identifying characteristics of NRRL B-18388.

* * * * *